(12) United States Patent
Lin

(10) Patent No.: US 7,678,301 B2
(45) Date of Patent: Mar. 16, 2010

(54) VESICLES OF HIGH MOLECULAR WEIGHT SILICONE POLYETHERS

(75) Inventor: Shaow Lin, Midland, MI (US)

(73) Assignee: Dow Corning Corporation, Midland, MI (US)

( * ) Notice: Subject to any disclaimer, the term of this patent is extended or adjusted under 35 U.S.C. 154(b) by 0 days.

(21) Appl. No.: 10/594,410

(22) PCT Filed: Apr. 19, 2005

(86) PCT No.: PCT/US2005/013327

§ 371 (c)(1),
(2), (4) Date: Sep. 26, 2006

(87) PCT Pub. No.: WO2005/102006

PCT Pub. Date: Nov. 3, 2006

(65) Prior Publication Data

US 2007/0166263 A1 Jul. 19, 2007

Related U.S. Application Data

(60) Provisional application No. 60/563,663, filed on Apr. 20, 2004, provisional application No. 60/620,999, filed on Oct. 21, 2004.

(51) Int. Cl.
*B01J 13/02* (2006.01)
*C08G 77/00* (2006.01)
(52) U.S. Cl. .................................... 264/4.1; 528/10
(58) Field of Classification Search .............. 424/70.12; 264/4.1
See application file for complete search history.

(56) References Cited

U.S. PATENT DOCUMENTS

| | | | |
|---|---|---|---|
| 2,823,218 A | 2/1958 | Speler et al. | |
| 3,957,842 A | 5/1976 | Prokai et al. | |
| 4,122,029 A | 10/1978 | Gee et al. | |
| 4,150,048 A | 4/1979 | Schilling, Jr. et al. | |
| 4,886,068 A | 12/1989 | Kaneko et al. | |
| 5,364,633 A | 11/1994 | Hill et al. | |
| 5,387,417 A | 2/1995 | Rentsch | |
| 5,393,452 A | 2/1995 | Raleigh et al. | |
| 5,411,744 A | 5/1995 | Hill et al. | |
| 5,472,686 A * | 12/1995 | Tsubaki et al. | ................. 424/59 |
| 5,478,860 A | 12/1995 | Wheeler et al. | |
| 5,620,684 A * | 4/1997 | Dupuis | .................... 424/70.12 |
| 5,623,017 A | 4/1997 | Hill | |
| 5,660,819 A | 8/1997 | Tsubaki et al. | |

(Continued)

FOREIGN PATENT DOCUMENTS

EP 0598531 5/1994

(Continued)

OTHER PUBLICATIONS

J. Newton et al.: "Silicone-Based Vesicle Delivery Systems" Cosmetics & Toiletries, vol. 119, No. 12, 2004, pp. 53-60.

(Continued)

*Primary Examiner*—Randy Gulakowski
*Assistant Examiner*—Robert Loewe
(74) *Attorney, Agent, or Firm*—Alan Zombeck

(57) ABSTRACT

Vesicle compositions from high molecular weight silicone polyether copolymers, methods for preparing the vesicle compositions, and personal, household, and healthcare formulations containing the vesicle compositions are disclosed.

1 Claim, 2 Drawing Sheets

Figure 1:
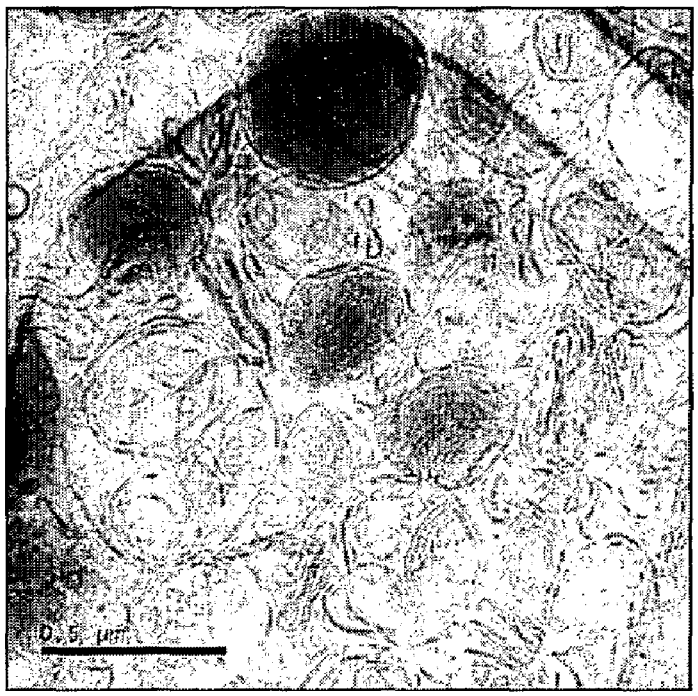

A Cryo-TEM image of the vesicle dispersion prepared for Example 8 from High DP silicone polyether (SPE1).

U.S. PATENT DOCUMENTS

| | | | |
|---|---|---|---|
| 5,660,853 | A | 8/1997 | Hansenne-Richoux |
| 5,705,562 | A | 1/1998 | Hill |
| 5,707,613 | A | 1/1998 | Hill |
| 5,741,518 | A | 4/1998 | Ribier et al. |
| 5,767,219 | A | 6/1998 | Takarada et al. |
| 5,811,487 | A | 9/1998 | Schulz, Jr. et al. |
| 5,869,727 | A | 2/1999 | Crane et al. |
| 5,919,487 | A * | 7/1999 | Simonnet et al. ............ 424/490 |
| 5,925,341 | A | 7/1999 | Cervantes et al. |
| 5,948,855 | A | 9/1999 | Lin et al. |
| 5,958,433 | A | 9/1999 | Simonnet |
| 5,958,448 | A | 9/1999 | Ekeland et al. |
| 6,017,546 | A * | 1/2000 | Glover ...................... 424/401 |
| 6,039,936 | A | 3/2000 | Restle et al. |
| 6,120,778 | A * | 9/2000 | Simonnet ................... 424/401 |
| 6,168,782 | B1 | 1/2001 | Lin et al. |
| 6,210,690 | B1 * | 4/2001 | Nabeshima et al. ......... 424/401 |
| 6,562,356 | B2 | 5/2003 | Verite et al. |
| 6,632,420 | B1 * | 10/2003 | Cen et al. ..................... 424/65 |
| 6,831,128 | B2 | 12/2004 | Altes et al. |
| 6,902,722 | B2 | 6/2005 | Candau et al. |
| 6,916,774 | B2 | 7/2005 | Trinh et al. |
| 6,998,424 | B2 | 2/2006 | Feng et al. |
| 7,041,630 | B1 | 5/2006 | Trinh et al. |
| 2002/0086935 | A1 | 7/2002 | Ferritto et al. |
| 2003/0032717 | A1 | 2/2003 | Ferritto et al. |
| 2003/0040571 | A1 | 2/2003 | Feng et al. |
| 2003/0050393 | A1 | 3/2003 | Ferritto et al. |
| 2003/0119779 | A1 * | 6/2003 | Maxon et al. .................. 514/52 |
| 2003/0171479 | A1 | 9/2003 | Lennon |
| 2003/0220425 | A1 | 11/2003 | Ferritto et al. |
| 2003/0224060 | A1 | 12/2003 | Simonnet et al. |
| 2004/0076652 | A1 | 4/2004 | Paspaleeva-Kuhn et al. |
| 2004/0077776 | A1 | 4/2004 | Feng et al. |
| 2004/0228821 | A1 | 11/2004 | Sunkel et al. |
| 2007/0166263 | A1 | 7/2007 | Lin |
| 2007/0217990 | A1 | 9/2007 | Lin |
| 2007/0219318 | A1 | 9/2007 | Lin et al. |
| 2007/0243241 | A1 | 10/2007 | Lin et al. |
| 2007/0256595 | A1 | 11/2007 | Nozoe |

FOREIGN PATENT DOCUMENTS

| | | |
|---|---|---|
| EP | 0483465 | 8/1995 |
| EP | 0523418 | 10/1998 |
| EP | 0724876 | 1/2000 |
| EP | 2000-313808 | 11/2000 |
| EP | 0780113 | 9/2002 |
| JP | 2000313808 | 11/2000 |
| WO | WO9906473 | 2/1999 |
| WO | WO0132146 | 5/2001 |
| WO | WO03010412 | 2/2003 |
| WO | WO03011948 | 2/2003 |
| WO | WO 03-101412 A2 | 12/2003 |
| WO | WO 2004-050045 A1 | 6/2004 |
| WO | WO 2005-102248 A2 | 11/2005 |
| WO | WO 2005-103117 A1 | 11/2005 |
| WO | WO 2005-103118 A1 | 11/2005 |
| WO | WO 2005-103157 A1 | 11/2005 |
| WO | WO2005102006 | 11/2005 |
| WO | WO2006028198 | 3/2006 |
| WO | WO2006091295 | 8/2006 |
| WO | WO2007053424 | 5/2007 |
| WO | WO2007100416 | 9/2007 |

OTHER PUBLICATIONS

Lin et al., U.S. Appl. No. 11/578,541 filed Oct. 16, 2006, Final Rejection Office Action, Examiner Olatunde S. Ojurongbe, dated May 15, 2009, confirmation No. 2399, art unit 1796.

* cited by examiner

A Cryo-TEM image of the vesicle dispersion prepared for Example 8 from High DP silicone polyether (SPE1).

A Cryo-TEM image of the vesicle dispersion prepared for Example 10 from High DP silicone polyether (SPE2).

VESICLES OF HIGH MOLECULAR WEIGHT SILICONE POLYETHERS

CROSS REFERENCE TO RELATED APPLICATIONS

This application is a U.S. national stage filing under 35 U.S.C. § 371 of PCT Application No. PCT/US05/013327 filed on 19 Apr. 2005, currently pending, which claims the benefit of U.S. Provisional Patent Application No. 60/563,663 filed 20 Apr. 2004 under 35 U.S.C. § 119 (e) and U.S. Provisional Patent Application No. 60/620,999 filed 21 Oct. 2004. PCT Application No. PCT/US05/013327 and U.S. Provisional Patent Application Nos. 60/563,663 and 60/620,999 are hereby incorporated by reference.

FIELD OF THE INVENTION

This application relates to vesicle compositions from high molecular weight silicone polyethers, methods for preparing the vesicle compositions, and personal, household, and healthcare formulations containing the vesicle compositions.

BACKGROUND OF THE INVENTION

The aggregation behavior of surfactants in aqueous media is a robust area of investigation. Various vesicle compositions, such as liposomes and the like, have been developed for many applications with particular emphasis on the design of such systems for delivery of active materials via a pharmaceutical or personal care product formulation. Long-standing needs in this field are to identify vesicle compositions that form and entrap actives easily, are stable under various chemical and mechanical stresses, and yet are able to deliver the actives in a controlled manner under desired conditions. To this end, many classes and types of surfactants have been investigated for their ability to form vesicles and thus entrap and deliver actives.

Vesicles derived from silicone surfactants, and more particularly silicone polyether surfactants, are of interest because of additional inherent benefits that this class of surfactants possesses vs other types. For example, silicone surfactants often have improved aesthetics in personal care formulations.

The aggregation behavior of certain silicone polyethers has been discussed along with their ability to form vesicles. For example, U.S. Pat. Nos. 5,364,633 and 5,411,744 by Hill teaches the self-assembly of certain silicone polyethers in aqueous media to form vesicles. PCT Application US2003/38455 by Lin teaches the entrapment of various oils in certain silicone polyether vesicles and their use in various personal care formulations.

While these references represent advancements in the art, a need still exists to create silicone vesicles having improved stability. For example, the silicone vesicles formed from the self-assembly procedures can lack durability. This lack of durability can limit the processing conditions they can be subject to in the formation of various finished products. Furthermore, such self-assembled silicone vesicles can lack the ability to provide sustained release of loaded actives over an extended period of time. Thus, a need exists for a process to prepare silicone vesicles having improved durability and the ability to release loaded actives over an extended period of time.

The present inventors have discovered that high molecular weight silicone polyethers (SPEs) form vesicle compositions in aqueous media. The vesicle compositions possess enhanced stability and are useful to prepare formulations for the delivery of personal, household, and healthcare active materials.

SUMMARY OF THE INVENTION

The present invention relates to vesicle compositions comprising a silicone polyether having a structure represented by:

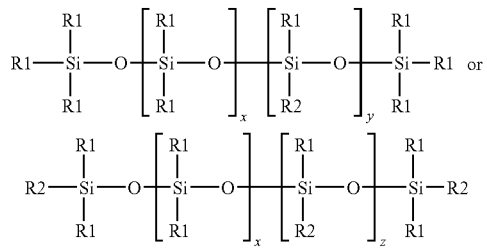

where R1 represents an alkyl group containing 1-6 carbon atoms; R2 represents the group $-(CH_2)_aO(C_2H_4O)_b(C_3H_6O)_cR3$; x is 251-1,000; y is 1-500; z is 1-500; a is 3-6; b is 4-20; c is 0-5; and R3 is hydrogen, a methyl group, or an acyl group.

The present invention further relates to a process for making a vesicle composition comprising;
I) combining,
   A) a silicone polyether copolymer, as described above,
   B) an optional water miscible volatile solvent,
   C) water,
   to form an aqueous dispersion of the silicone polyether copolymer,
II) mixing the aqueous dispersion to form the vesicle composition,
III) optionally, removing the water miscible volatile solvent from the vesicle composition.

Furthermore, the present invention relates to personal, household, and healthcare formulations containing the vesicle compositions.

DETAILED DESCRIPTION OF THE INVENTION

The vesicle compositions of the present invention comprise a silicone polyether having an average structure represented by:

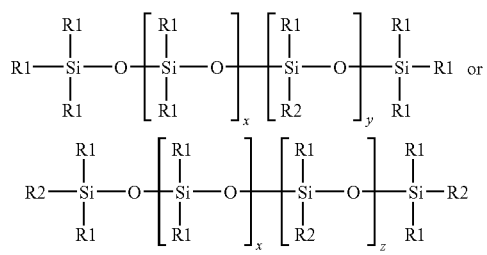

In these structures, R1 represents an alkyl group containing 1-6 carbon atoms such as methyl, ethyl, propyl, butyl, pentyl, and hexyl; R2 represents the group $-(CH_2)_aO(C_2H_4O)_b(C_3H_6O)_cR3$; x has a value of 251-1,000, alternatively 251-750, or alternatively 251-500; y has a value of 1-500, alternatively 1-100, or alternatively 2-50; z has a value of 1-500, or alternatively 1-100; m has a value of 3-5; n is one; a has a value of 3-6; b has a value of 4-20; c has a value of 0-5; and R3 is hydrogen, a methyl group, or an acyl group such as acetyl. Typically, R1 is methyl; b is 6-12; c is zero; and R3 is hydrogen.

As used herein, "vesicle" is the common art term referring to entities formed from the aggregation of surfactant and/or lipid molecules in aqueous medium, characterized by the presence of one or more walls or membranes formed from a surfactant and/or lipid compound creating one or more internal voids. The walls or membranes formed by the surfactant and/or lipid in vesicles can be unilamellar, bilamellar, oligolamellar, or multilamellar structures. The formation of vesicles can be confirmed by techniques common in the state of the art. Typically, the lamellar phase structure in vesicles exhibit birefringence when examined with a cross polarizing microscope. Alternatively, the formation of vesicles can be demonstrated by Cyro-Transmission Electron Microscopy (Cryo-TEM) techniques.

The silicone polyethers useful to prepare the vesicle compositions of the present invention can be prepared by any method known in the art for preparing such copolymers. Typically however, the SPEs useful in the preparation of the vesicle compositions of the present invention are obtained by reacting an SiH containing organopolysiloxane with a polyoxyethylene having an unsaturated hydrocarbon group at a molecular terminal, in a hydrosilylation reaction. Typically, the molar ratio of the unsaturated hydrocarbon groups to SiH in the reaction is at least 1:1.

The vesicle compositions of the present invention can be prepared by mixing the SPEs with water using any technique known in the state of the art for creating vesicle compositions. The type and extent of the mixing technique will depend on the specific structure of the SPE chosen. Typically, the formation of vesicles from the SPEs of the present invention will require the presence of a water soluble solvent to facilitate the formation of vesicles. In a preferred embodiment, the vesicle compositions of the present invention are prepared using a process comprising;

I) combining,
  A) a silicone polyether having a structure represented by:

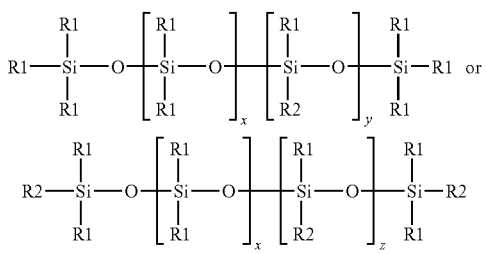

where R1 represents an alkyl group containing 1-6 carbon atoms;
R2 represents the group —$(CH_2)_aO(C_2H_4O)_b(C_3H_6O)_cR3$;
x is 251-1,000; y is 1-500; z is 1-500; a is 3-6; b is 4-20; c is 0-5;
and R3 is hydrogen, a methyl group, or an acyl group,
B) a water miscible volatile solvent,
C) water,
to form an aqueous dispersion of the silicone polyether copolymer, II) mixing the aqueous dispersion to form vesicle composition,
III) optionally, removing the water miscible volatile solvent from the vesicle composition.

The silicone polyether, component A), is the same as described above.

Component B) is a water-miscible volatile solvent. As used herein "water-miscible" means the solvent forms a dispersion with water at room temperature for at least several hours. "Volatile" means the solvent has a higher vapor pressure than water at various temperatures. As such, when the aqueous dispersion of the organopolysiloxane and solvent are subjected to conditions to remove the solvent, such as heating the dispersion under reduced pressures, the solvent is primarily removed first, allowing all or most of the water to remain in the composition.

Suitable water-miscible volatile solvents for vesicle dispersion preparation include organic solvents such as alcohols, ethers, glycols, esters, acids, halogenated hydrocarbons, diols. The organic solvents should be miscible with water at the proportion and lower in order to effectively disperse silicones and maintain stable and uniform dispersion overtime. For the purpose of illustration, water-miscible alcohols include methanol, ethanol, propanol, isopropanol, butanol, and higher hydrocarbon alcohols; ethers include gylcol ethers, methyl-ethyl ether, methyl isobutyl ether (MIBK), etc; glycols include propylene glycols, esters include esters of triglycerol, the esterification products of acid and alcohol; halogenated hydrocarbons include chloroform. Typically water-miscible organic solvents are solvents with relatively low boiling points (<100° C.) or high evaporation rate, so they may be removed under vacuum with ease. The most preferred water-miscible organic solvents for this invention are volatile alcohols including methanol, ethanol, isopropanol, and propanol. These alcohols can be removed from aqueous mixtures containing silicone vesicle dispersions via vacuum stripping at ambient temperature.

The order of combining components A), B), and C) is not critical, but typically A) and B) are first mixed and then water added to the mixture. There are no special requirements or conditions needed for effecting the mixing of components A), B), and C). The mixing can be conducted in a batch, semi-continuous, or continuous process.

The amount of components A), B), and C) can vary in the process, but typically range as follows;
  A) 2 to 50 wt %, alternatively 2 to 25 wt %, or alternatively 2 to 15 wt %,
  B) 0 to 50 wt %, alternatively 2 to 30 wt %, or alternatively 2 to 20 wt %,
  C) sufficient amount to provide the sum of the wt % of A), B), and C) to equal 100%

The amount of B) water-miscible volatile solvent used to disperse the SPE depends on the type of organopolysiloxane and how much hydrophilic groups are present. Typically, the aqueous mixture to effective disperse silicones comprises of 5 to 80 parts of solvent and 20 to 95 parts of water; alternatively 5 to 50 parts of water, or alternatively 10 to 40 parts water.

Step II in the process of the present invention is mixing the aqueous dispersion formed in Step I to form vesicles. There are no special requirements or conditions needed to effect the mixing and formation of vesicles. Mixing techniques can be simple stirring, homogenizing, sonalating, and other mixing techniques known in the art to effect the formation of vesicles in aqueous dispersions. The mixing can be conducted in a batch, semi-continuous, or continuous process.

The formation of vesicles can be confirmed by techniques common in the state of the art. Typically, vesicles have a lamellar phase structure which exhibit birefringence when examined with a cross polarizing microscope. Alternatively, the formation of vesicles can be demonstrated by Cyro-Transmission Electron Microscopy (Cryo-TEM) techniques. Particle size measurements can also be used to indicate that the organopolysiloxanes are sufficiently dispersed in aqueous medium typical of vesicle sizes. For example, average particle sizes of less than 0.500 µm (micrometers), are typical for dispersed vesicles. Vesicles having an average particle size of less than 0.200 µm, or 0.100 µm are possible with the teachings of the present invention.

Step III in the process of the present invention is optional, and involves removing the water miscible volatile solvent, component B). Typically, the water miscible volatile solvent is removed by known techniques in the art, such as subjecting the vesicle composition to reduced pressures, while optionally heating the composition. Devices illustrative of such techniques include rotary evaporators and thin film strippers.

The present invention also relates to the vesicle compositions produced by the methods, as described supra. The formation of vesicles can be confirmed by techniques common in the state of the art. Typically, vesicles having a lamellar phase structure which exhibit birefringence when examined with a cross polarizing microscope. Alternatively, the formation of vesicles can be demonstrated by Cyro-Transmission Electron Microscopy (Cryo-TEM) techniques. Particle size measurements can also be used to indicate that the organopolysiloxanes are sufficiently dispersed in aqueous medium typical of vesicle sizes For example, average particle sizes of less than 0.500 µm (micrometers), are typical for dispersed vesicles. Vesicles having a average particle size of less than 0.200 µm, or 0.100 µm are possible with the method of the present invention.

The present invention also relates to vesicle compositions further comprising a personal, household, or health care ingredient. Thus, the vesicle compositions can be used to entrap, and subsequently deliver after application, a personal, household care, or health care ingredient. A listing of possible personal, household, or health care ingredients is taught in WO 03/101412, which is incorporated herein by reference. The personal or health care ingredient can also be selected from a personal or health care "active", that is, any compound known to have either cosmetic and/or pharmaceutical activity. A representative listing of such personal or health care actives are disclosed in U.S. Pat. No. 6,168,782, which is hereby incorporated by reference.

Compositions prepared according to the invention can be used in various over-the-counter (OTC) personal care compositions, health care compositions, and household care compositions, but especially in the personal care arena. Thus, they can be used in antiperspirants, deodorants, skin creams, skin care lotions, moisturizers, facial treatments such as acne or wrinkle removers, personal and facial cleansers, bath oils, perfumes, colognes, sachets, sunscreens, pre-shave and after-shave lotions, liquid soaps, shaving soaps, shaving lathers, hair shampoos, hair conditioners, hair sprays, mousses, permanents, depilatories, hair cuticle coats, make-ups, color cosmetics, foundations, blushes, lipsticks, lip balms, eyeliners, mascaras, oil removers, color cosmetic removers, nail polishes, and powders.

EXAMPLES

The following examples are presented to further illustrate the compositions and methods of this invention, but are not to be construed as limiting the invention. All parts and percentages in the examples are on a weight basis and all measurements were obtained at 23° C., unless indicated to the contrary.

Materials

Representative high molecular weight silicone polyethers, useful in the vesicle compositions of the present invention, were prepared by the hydrosilylation of high molecular weight methyl-hydrogen polysiloxanes (designated as $MD_xD'_yM$ in which x designates the number of dimethyl siloxy units, and y the number of methyl-hydrogen siloxy units respectively) with a monoallyloxy polyoxyethylene having a $M_w$ of 500 (AE501 Dow Chemical, Midland Mich.) using well known techniques.

As used in the examples herein, SPE1 denotes the silicone polyether prepared from the reaction of $MD_{260}D'_{15}M$ with AE501, and SPE2 the silicone polyether prepared from the reaction of $MD_{520}D'_{30}M$ with AE501.

Testing Procedures

Cyro-Transmission Electron Microscopy (TEM)

The vesicle compositions were analyzed via Cyro-TEM techniques according to the following procedure. Around 2.3 µl of aqueous sample solution was loaded using a micropipette on a lacey carbon film coated Cu TEM grid that was cleaned and rinsed with acetone and chloroform. The samples were diluted to 5% solution with de-ionized water. The excess fluid on the grid surface was removed by blotting the surface with a filter paper for 1.5 second to make an aqueous thin film for TEM. The grid was then plunged into a liquid ethane contained in a small vessel located in a larger liquid nitrogen vessel under −175° C. atmosphere in the cryo-plunge system to vitrify the water film on the grid and to avoid water crystallization. The quenched sample grid was transferred in to the cryo-grid box in the cryo-plunge system. The grid box containing the sample was transferred into a Gatan cryo-transfer system filled with liquid nitrogen and loaded in a cryo-TEM stage, which has been positioned in the cryo-transfer system and cooled down to below −160° C. The sample was loaded in TEM (JEOL 2000FX) and the images were observed at below −160° C. A much colder finger, cooled to −180° C. in TEM using liquid nitrogen, was present to reduce any possible contamination on the cold specimen surface under high vacuum during TEM analysis. The digital images, as shown herein, were taken using a Gatan CCD camera attached at the bottom of the TEM column and Digital Micrograph software.

Example 1-3

A vesicle dispersion was successfully prepared by dispersing 44.3 g of SPE1 in a mixture of 73.77 g ethanol and 165.39 g water. A uniform dispersion with milky appearance was observed. The average particle size was 0.274 µm, as summarized in Table 1 as Example 1.

A uniform dispersion with even smaller particle size was made from SPE1 by further homogenizing through a high pressure, high shear unit like Microfluidizer, summarized in Table 1 as Example 2.

A stable dispersion of SPE1 with small particle size in largely water was prepared by further stripping off the volatile alcohol solvent. As shown by Example 3 in Table 1, the final dispersion has a composition of 20% SPE vesicles, 5% alcohol and 75% water.

TABLE 1

|  | Example | | |
| --- | --- | --- | --- |
|  | 1 | 2 | 3 |
| Dispersion type | Neat SPE | Neat SPE | Neat SPE |
| Mix Method | Mixed | Mixed, MicroFluidized | Microfluidized, stripped |
| EtOH, g | 73.770 | 73.770 | 26.49 |
| SPE1 g | 44.280 | 44.280 | 15.89 |
| De-ionized water, g | 165.39 | 165.39 | 59.37 |
| Batch, before strip, g |  |  | 101.75 |
| Volatiles Removed, g |  |  | 22.6 |
| Final batch size, g | 283.4 | 283.4 | 79.1 |
| Wt. % SPE1 | 15.62 | 15.62 | 20.09 |
| Wt. % Alcohol | 26.03 | 26.03 | 4.87 |
| Wt. % Water | 58.35 | 58.35 | 75.04 |
| Appearance | Milky, uniform dispersion | Hazy to cloudy dispersion | Cloudy dispersion |
| Average particle, μm | 0.274 | 0.0945 | 0.1011 |
| D(v, 0.5), μm | 0.2687 | 0.0830 | 0.0918 |
| D(v,, 0.9), μm | 0.361 | 0.1539 | 0.1624 |
| Peak 1, diameter, μm | 0.2687 | 0.0830 | 0.0918 |
| Peak 1, volume % | 100% | 100% | 100% |

Examples 4-6

Vitamin A Palmitate Entrapped in High DP SPE Vesicle Dispersion

The following examples show vitamin A palmitate can be incorporated into high DP SPEs stable vesicles in water dispersions.

A uniform dispersion was prepared by mixing 9.74 g of vitamin A palmitate with 44.74 g of SPE1 and isopropanol and ethanol, as described in Table 2, Example 4. Water was incorporated and mechanically mixed to form a uniform dispersion. The final mixture was a yellowish dispersion with average particle size of 0.367 μm.

The vitamin A palmitate entrapped SPE dispersion can be further reduced in particle size by passing through a high pressure, high shear processor like Microfluidizer, as described by Example 5 in Table 2. The final dispersion was a smooth, yellowish dispersion with average particle size of about 0.137 μm.

The vitamin A palmitate entrapped SPE dispersion can be made stable in an aqueous mixture with minimal alcohol present. As illustrated in Table 2, the volatile alcohols in the formulation of Example 2 were stripped off under vacuum at ambient temperature. The final dispersion is summarized as Example 6 in Table 2. The dispersion was a smooth, uniform light yellowish dispersion with average particle size of 0.156 μm.

TABLE 2

|  | Example # | | |
| --- | --- | --- | --- |
|  | 4 | 5 | 6 |
| Mix Method | Mixed | Mixed, MicroFluidized | Microfluidized, stripped |
| Vitamin A Palmitate, g | 9.74 | 9.74 | 6.82 |
| Isopropanol, g | 9.74 | 9.74 | 6.86 |
| EtOH, g | 69.5 | 69.5 | 48.82 |
| SPE1, g | 44.74 | 44.74 | 31.42 |
| De-ionized water, g | 165.15 | 165.15 | 115.98 |
| Batch, before strip, g |  |  | 209.88 |
| Volatiles Removed, g |  |  | 55.2 |
| Final batch size, g | 298.86 | 298.86 | 154.7 |
| Wt. % SPE Polymer | 14.97 | 14.97 | 20.31 |
| Wt. % VAP | 3.25 | 3.25 | 4.41 |
| Wt. % Alcohol | 26.52 | 26.52 | 0.31 |
| Wt. % Water | 55.26 | 55.26 | 74.97 |
| Appearance | Dull yellow dispersion | Pale yellow, smooth | Smooth milky yellow |
| Average particle, μm | 0.367 | 0.1371 | 0.1557 |
| D(v, 0.5), μm | 0.353 | 0.1234 | 0.1426 |
| D(v,, 0.9), μm | 0.514 | 0.2279 | 0.2349 |
| Peak 1, diameter, μm | 0.353 | 0.1234 | 0.1426 |
| Peak 1, volume % | 100% | 100% | 100% |

Examples 7-10

Figure 2:
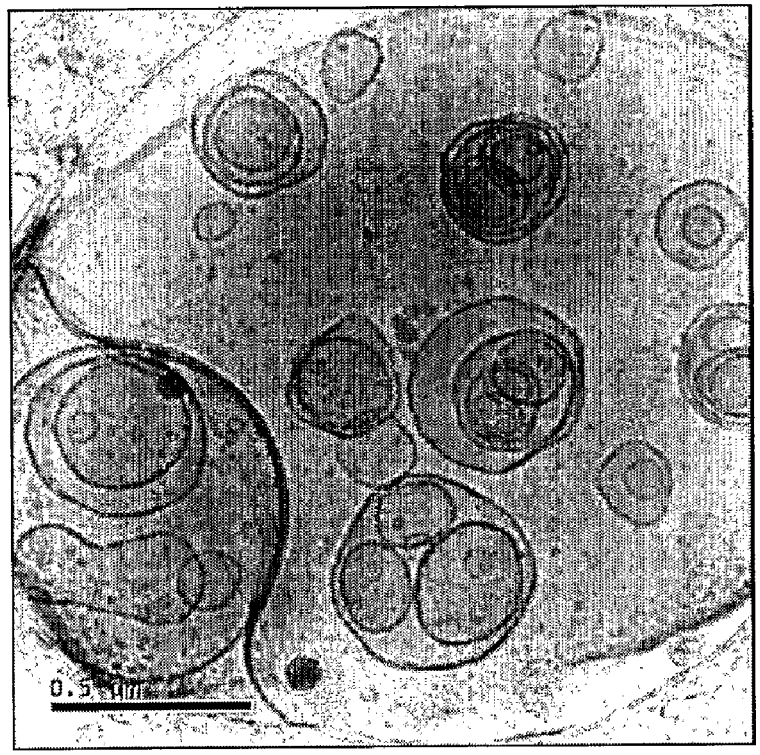

Two sets of vesicle dispersions were prepared for Cyro-TEM evaluations, following similar procedures as described in the examples above. The formulations for the vesicle dispersions are summarized in Tables 3 and 4. The Cryo-TEM images are shown in FIGS. 1 and 2.

TABLE 3

|  | Example | |
| --- | --- | --- |
|  | 7 | 8 |
| Process History | As Made | Mixed, then stripped |
| SPE1, g | 25.36 | 22.84 |
| IPA, g | 75.47 | 67.96 |
| Water, g | 150.22 | 135.27 |
| Batch size before strip, g | 251.05 | 226.06 |
| Volatile removed, g |  | 68.05 |
| Batch size after strip, g |  | 158.01 |
| Vesicle dispersion composition |  |  |
| % SPE1 | 10.1 | 14.5 |
| % Alcohol | 30.1 | 0.0 |
| % Water | 59.8 | 85.5 |
| Dispersion appearance | water-white clear | milky dispersion |
| Average particle size Mv, μm | 0.0314 | 0.591 |
| D(v, 0.5), μm | 0.02977 | 0.508 |
| D(v, 0.9), μm | 0.044 | 1.078 |

TABLE 4

|  | Example | |
| --- | --- | --- |
|  | 9 | 10 |
| Process History | Mixed | Mixed, then stripped |
| SPE2 g | 25.28 | 22.88 |
| IPA, g | 75.28 | 68.12 |
| Water, g | 150.15 | 135.87 |
| Batch size before strip, g | 250.71 | 226.86 |
| Volatile removed, g |  | 69.31 |
| Batch size after strip, g |  | 157.55 |
| Vesicle dispersion composition |  |  |
| Wt. % SPE | 10.1 | 14.5 |
| Wt. % Alcohol | 30.0 | 0.0 |
| Wt. % Water | 59.9 | 85.5 |
| Dispersion appearance | Water-white clear | Milky dispersion |
| Average particle size Mv, μm | 0.0372 | 0.973 |
| D(v, 0.5), μm | 0.02532 | 0.672 |
| D(v, 0.9), μm | 0.0376 | 2.116 |

The invention claimed is:

1. A process for making a vesicle composition comprising;
I) combining,
   A) 2 to 25 wt % of a silicone polyether copolymer having a structure represented by:

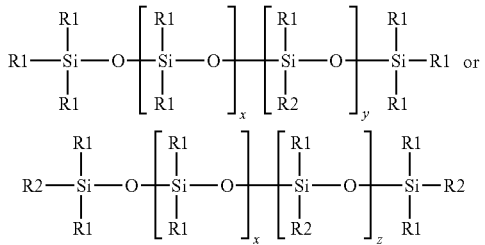

where R1 represents an alkyl group containing 1-6 carbon atoms;
   R2 represents the group $-(CH_2)_aO(C_2H_4O)_b(C_3H_6O)_cR3$;
   x is 251-1,000; y is 1-500; z is 1-500; a is 3-6; b is 4-20; c is 0-5;
   and R3 is hydrogen, a methyl group, or an acyl group,
   B) 2 to 30 wt % of a water miscible volatile solvent,
   C) water in a sufficient amount to provide the sum of the wt % of A), B), and C) to equal 100%,
   to form an aqueous dispersion of the silicone polyether copolymer,
II) mixing the aqueous dispersion to form a vesicle composition having an average particle size of less than 0.500 micrometers,
III) removing the water miscible volatile solvent from the vesicle composition.

* * * * *